United States Patent
Pinter et al.

(10) Patent No.: US 10,764,339 B2
(45) Date of Patent: *Sep. 1, 2020

(54) SYSTEMS AND METHODS FOR DYNAMIC BANDWIDTH ALLOCATION

(71) Applicant: INTOUCH TECHNOLOGIES, INC., Goleta, CA (US)

(72) Inventors: Marco Pinter, Santa Barbara, CA (US); Justin Chan, Mercer Island, WA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/284,916

(22) Filed: Feb. 25, 2019

(65) Prior Publication Data

US 2019/0190965 A1    Jun. 20, 2019

Related U.S. Application Data

(63) Continuation of application No. 15/013,656, filed on Feb. 2, 2016, now Pat. No. 10,218,748, which is a
(Continued)

(51) Int. Cl.
| | |
|---|---|
| *H04L 29/06* | (2006.01) |
| *H04L 12/26* | (2006.01) |
| *G06F 19/00* | (2018.01) |
| *H04M 3/56* | (2006.01) |
| *H04N 7/15* | (2006.01) |
| *H04N 7/14* | (2006.01) |
| *G16H 40/63* | (2018.01) |

(52) U.S. Cl.
CPC ...... *H04L 65/1086* (2013.01); *G06F 19/3418* (2013.01); *G16H 40/63* (2018.01); *H04L 43/02* (2013.01); *H04L 65/1059* (2013.01); *H04L 65/403* (2013.01); *H04L 65/80* (2013.01); *H04M 3/567* (2013.01); *H04N 7/148* (2013.01); *H04N 7/15* (2013.01)

(58) Field of Classification Search
CPC . H04L 65/1086; H04L 65/1059; H04L 65/80; H04L 43/02; G16H 40/63; G06F 19/3418; H04M 3/567; H04N 7/148; H04N 7/15
USPC ........................................................ 709/232
See application file for complete search history.

(56) References Cited

U.S. PATENT DOCUMENTS

2006/0251116 A1*  11/2006  Bedingfield, Sr. .......................... H04L 41/0896
370/468
2009/0129405 A1*  5/2009  Lauwers ............. H04L 65/1066
370/468
(Continued)

*Primary Examiner* — James E Springer

(57) ABSTRACT

Disclosed herein are various embodiments of systems and methods that may be utilized in a variety of videoconferencing applications. According to various embodiments, techniques may be utilized to dynamically allocate and adjust bandwidth utilization during a videoconferencing session. A data network may allow for the transmission of data between two or more endpoints. The data exchanged between the endpoints may include video data, audio data, control data, and status data. Control data may be utilized in various embodiments to operate a robotic videoconferencing endpoint. Accordingly, various components of a data network connecting videoconferencing endpoints may transmit data wirelessly.

8 Claims, 8 Drawing Sheets

Related U.S. Application Data continuation of application No. 12/959,550, filed on Dec. 3, 2010, now Pat. No. 9,264,664.

(56) References Cited

U.S. PATENT DOCUMENTS

| | | | | |
|---|---|---|---|---|
| 2011/0122869 A1* | 5/2011 | Jefremov | ............ | H04L 43/0894 370/352 |
| 2012/0115433 A1* | 5/2012 | Young | ................ | H04L 41/5029 455/406 |

* cited by examiner

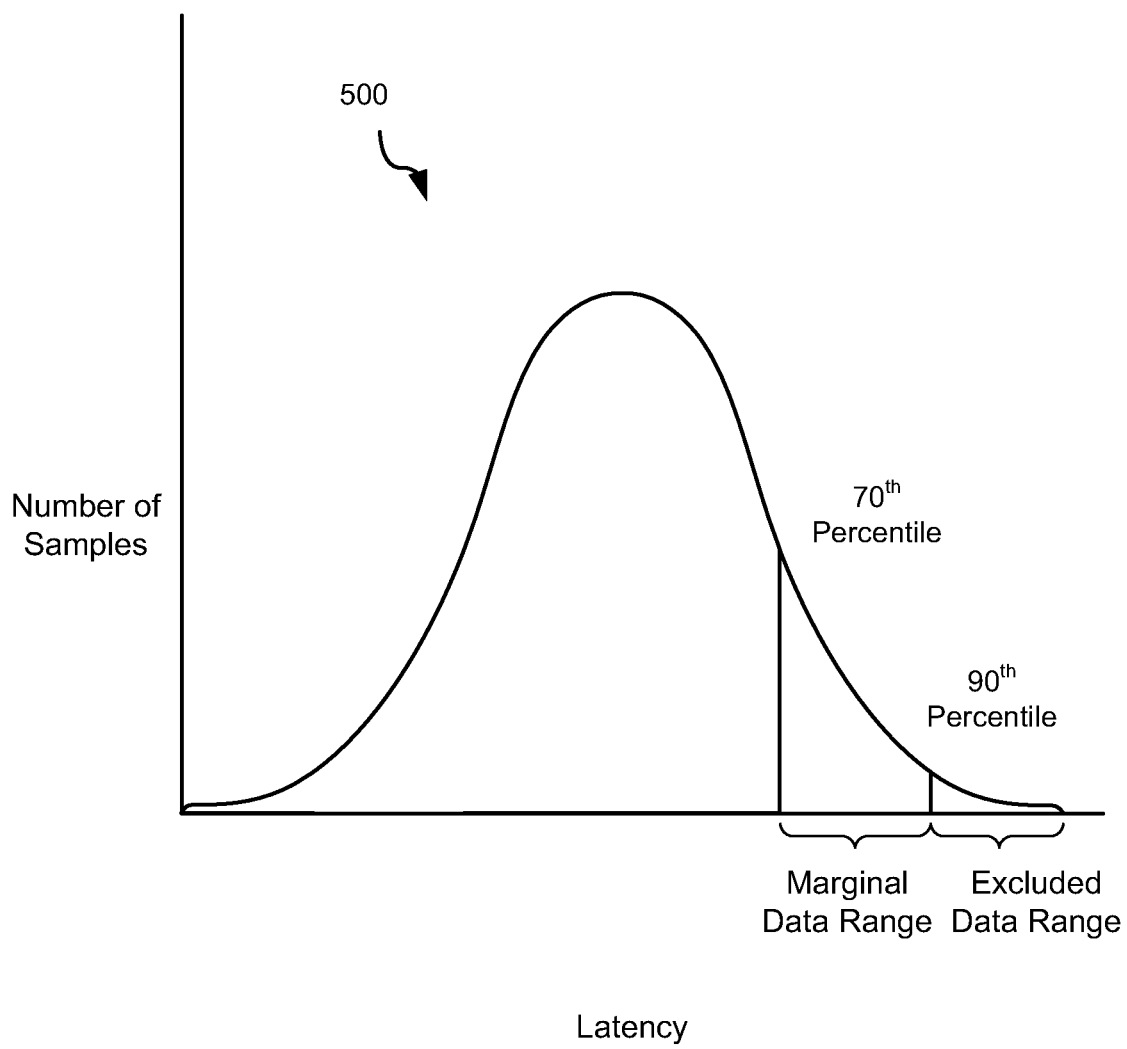

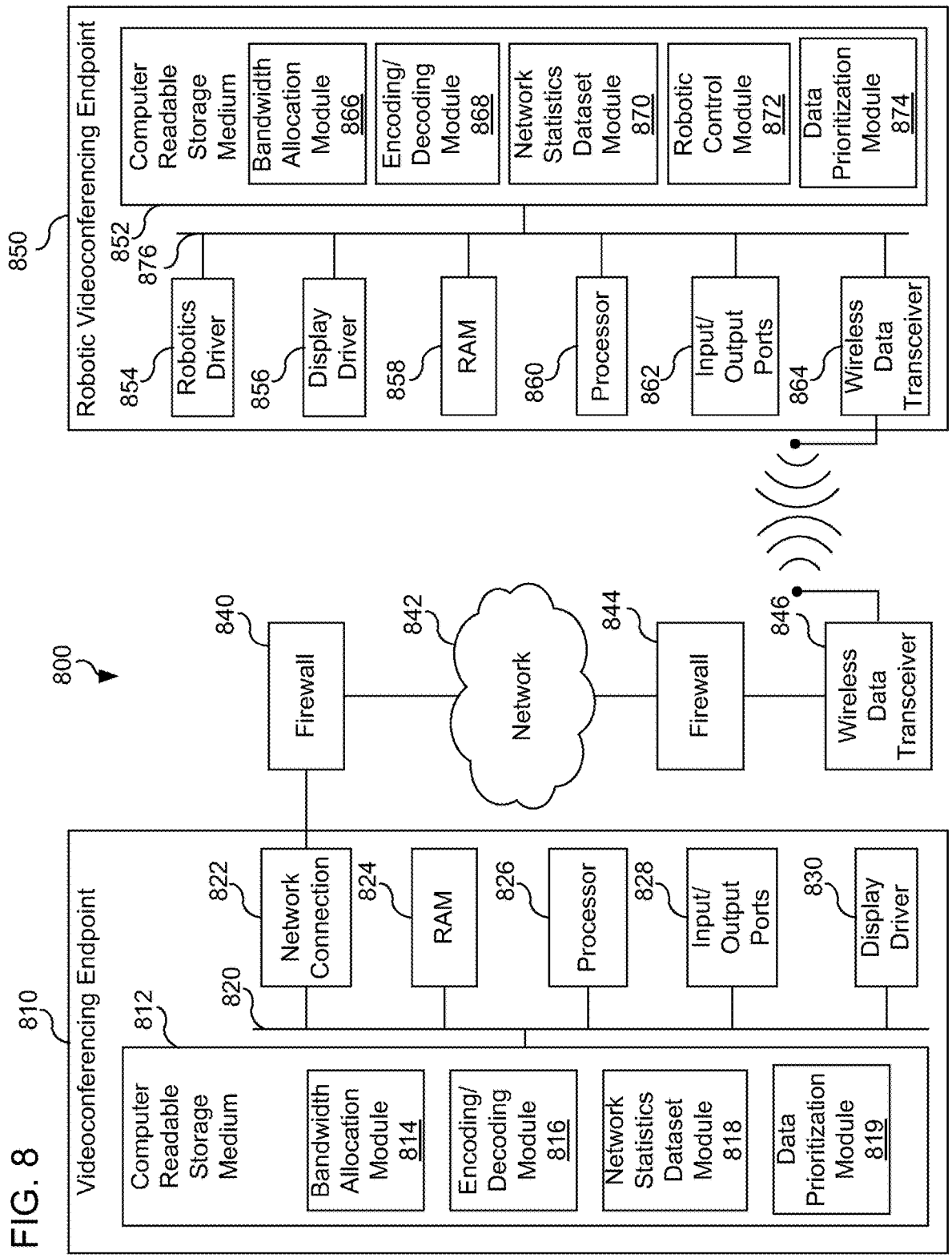

SYSTEMS AND METHODS FOR DYNAMIC BANDWIDTH ALLOCATION

BRIEF DESCRIPTION OF THE DRAWINGS

FIG. 5A illustrates an exemplary distribution comprising a plurality of data samples and specified boundaries that may be used in processing newly obtained data samples.

FIG. 8 illustrates a functional block diagram of a videoconferencing endpoint.

DETAILED DESCRIPTION OF PREFERRED EMBODIMENTS

Figure 1:
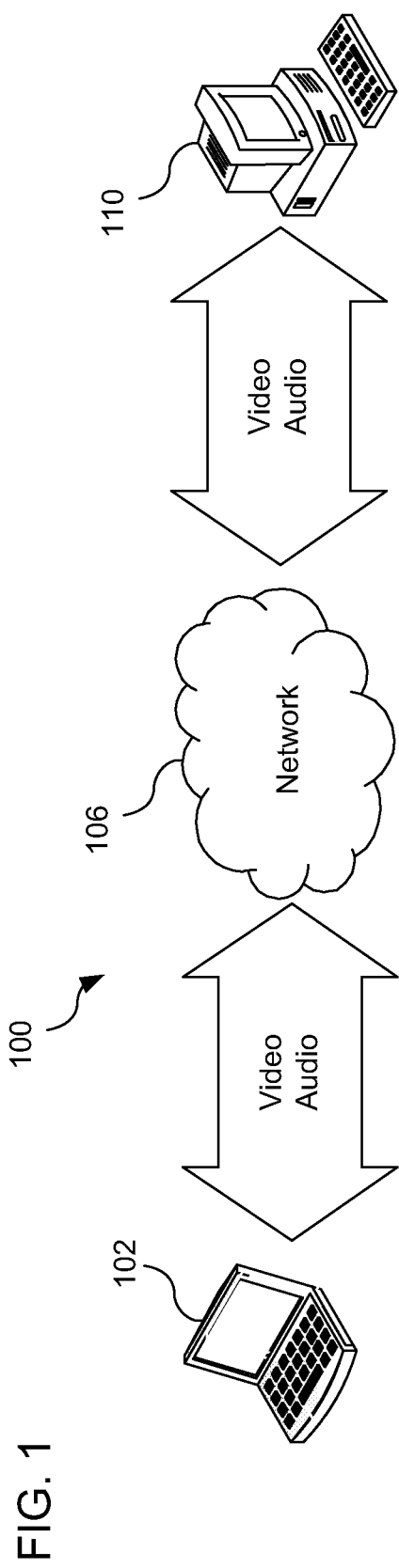
FIG. 1 illustrates a functional block diagram of one embodiment of a videoconferencing system, which may utilize various techniques for dynamically adjusting bandwidth utilization between two endpoints.

Disclosed herein are various embodiments of systems and methods that may be utilized in a variety of videoconferencing applications. According to various embodiments, techniques may be utilized to dynamically allocate and adjust bandwidth utilization during a videoconferencing session.

A data network may allow for the transmission of data between two or more endpoints. The data exchanged between the endpoints may include video data, audio data, control data, and status data. Control data may be utilized in various embodiments to operate a robotic videoconferencing endpoint. Accordingly, various components of a data network connecting videoconferencing endpoints may transmit data wirelessly. Status data may refer to any type of data that is not video data, audio data, or control data.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. In particular, an "embodiment" may be a system, an article of manufacture (such as a computer readable storage medium), a method, and a product of a process.

The phrases "connected to," and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless specified to require an order.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

FIG. 1 illustrates a diagram of one embodiment of a videoconferencing system 100, which may utilize various techniques disclosed herein for dynamically adjusting bandwidth utilization between two endpoints 102 and 110. Endpoint 102 is in communication with endpoint 110 via network 106. Each of endpoints 102 and 110 generate audio and video data, which is transmitted via network 106. Each of endpoints 102 and 110 also receive audio and video data. The audio and video data received by each of endpoints 102 and 110 may allow users of the respective endpoints to communicate visually and audibly.

Data network 106 represents any type of data network that may facilitate data communication between endpoints 102 and 110. For example, network 106 may comprise a local area network or a wide area network. Network 106 may comprise an intranet, a virtual private network, or a public network, such as the Internet or other data communications networks (e.g., cellular data networks). Network 106 may further comprise routers, gateways, firewalls, wireless network adapters, and other types of networking equipment.

Various types of endpoints are contemplated, including fixed and mobile videoconferencing endpoints. In embodiments having one or more mobile endpoints, various wireless technologies may be utilized in order to allow the mobile endpoint to remain in data communication with network 106. Various embodiments disclosed herein may be utilized in connection with robotic systems employed for a variety of applications. One such embodiment is illustrated in FIG. 2.

Figure 2:
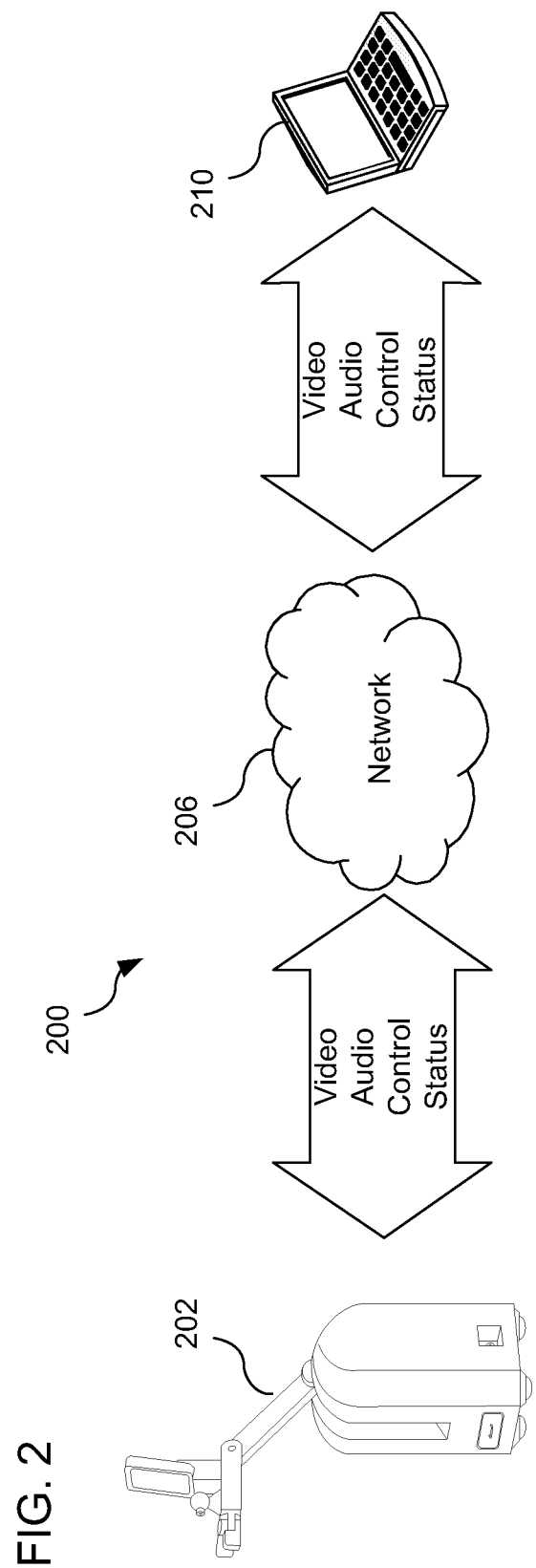
FIG. 2 illustrates a functional block diagram of one embodiment of a system, which may utilize various techniques for dynamically adjusting bandwidth utilization between two endpoints.
Figure 3:
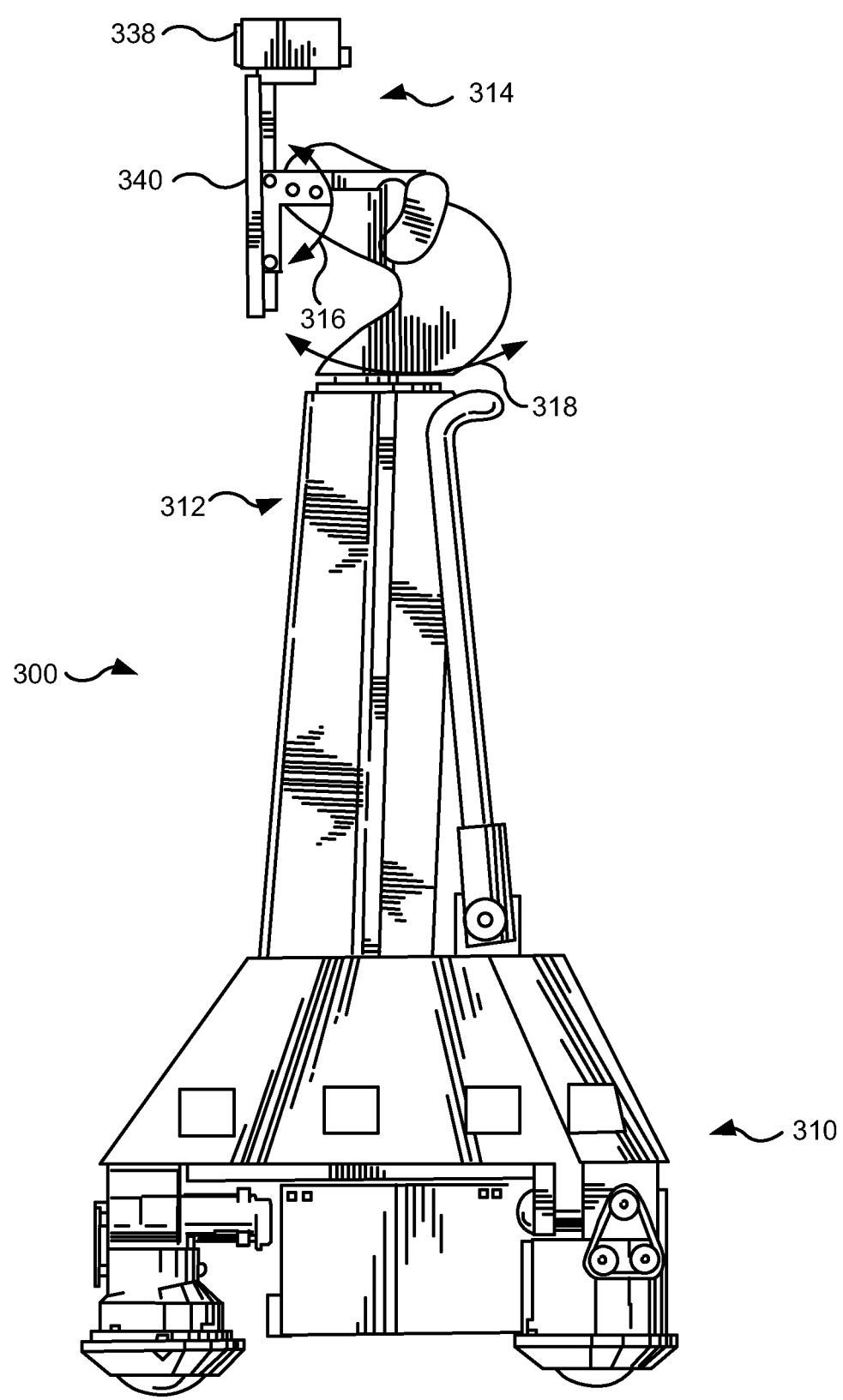
FIG. 3 illustrates a perspective view of one embodiment of a robotic videoconferencing endpoint.

FIG. 2 illustrates a functional block diagram of a system 200, which may utilize various techniques disclosed herein for dynamically adjusting bandwidth utilization between two endpoints. An endpoint 202, which is illustrated and described in greater detail in connection with FIG. 3, is in communication with an endpoint 210 via a data network 206. Each of endpoints 202 and 210 may comprise suitable network adapters to enable transmission to, and receipt of data from, data network 206.

Endpoints 202 and 210 exchange a variety of types of data, including video data, audio data, control data, and status data via data network 206. Data network 206 represents any type of data network that may facilitate data communication between endpoints 202 and 210. For example, network 206 may comprise a local area network or a wide area network. Network 206 may comprise an intranet, a virtual private network, or a public network, such as the Internet or other data communications networks (e.g., cellular data networks). Network 206 may further comprise routers, gateways, firewalls, wireless network adapters, and other types of networking equipment.

System 200 may be employed, for example, by a medical practitioner or other care provider to monitor individuals at a remote location. According to various embodiments, data prioritization schemes may be employed so that higher priority data is transmitted with greater reliability or at a higher data rate than lower priority data. For example, in system 200 control data transmitted from second endpoint 210 to first endpoint 202 may be designated as high priority data. Such a prioritization may allow a user to remain in control of the motion of endpoint 202, even if network throughput is reduced. Status data, which may include telemetry data gathered from a patient (e.g., pulse rate, EKG, oxygenation, etc.), may also be designated as relatively high priority data. Audio data may be prioritized before video data, such that a medical practitioner and patient can maintain audible communication. Finally, video data may be transmitted using the lowest priority. According to various embodiments, audio data and video data variable compression schemes may be utilized in order to more efficiently utilize available bandwidth. During periods of decreased network throughput, a higher compression ratio may be utilized for video and/or audio data. Such compression may reduce the quality of the video and/or audio data; however, such compression may allow for continued use of system 200 even if data throughput is reduced. In still other embodiments, a video frame rate may be adjusted dynamically, prior to segmenting the data into packets. According to various embodiments, status data comprising information gathered from patient sensors (e.g. an EKG sensor, a blood oxygenation sensor, etc.) may receive the highest priority.

The data transmitted between endpoints 202 and 210 may be asymmetrical in quantity and/or priority. For example, in telemedicine applications, data flowing from the remote station to the robot is less critical than video and data flowing from endpoint 202 to endpoint 210. Various embodiments of system 200 may allow dynamic adjustment of bandwidth, such that the minimum allowable bandwidth from one endpoint is higher than the minimum allowable bandwidth from the other endpoint. For example, the allowable outgoing data rate from endpoint 210 may be in the range of 150 kbps to 700 kbps, but the allowable outgoing data rate from endpoint 202 may be in the range of 200 kbps to 700 kbps. For example, a data rate of less than 200 kbps may make diagnosis problematic and impede the ability to drive a robotic videoconferencing endpoint.

According to various embodiments, data may be prioritized at the application layer. According to such embodiments, the application generating video and audio and control/sensor data may be aware of the available bandwidth and may adjust the content to be transmitted accordingly. Such an application may allow for a user to customize settings to be used during a particular session or at various points within a session. For example, in one embodiment where an endpoint is used in telemedicine applications, the quality images received from an endpoint near a patient may be assigned a higher priority, depending on whether a diagnosis is made using the images. For example, if a dermatologist is utilizing a videoconferencing endpoint to obtain images of a rash on a patient's skin, image quality may be assigned a greater importance than other characteristics (e.g., a video frame rate). In another example, a physician counseling with the patient may not be relying on images to provide a diagnosis. In this example, audio data may receive a high priority, so that audio communications between the patient and physician are maintained even if network throughput declines. In still another example, during a videoconferencing session a physician may drive a robotic videoconferencing endpoint from one location in a medical facility to another location. While the videoconferencing endpoint is in motion, frame rate may be assigned a higher priority than image quality, such that a remote driver is better able to control the movement of the robotic videoconferencing endpoint. According to various embodiments, a robotic videoconferencing endpoint may be configured such that upon detection of base motion, prioritization switches from image quality to frame rate.

FIG. 3 illustrates a perspective view of one embodiment of a robotic videoconferencing endpoint 300. Videoconferencing endpoint 300 may include a robotic platform 310 that is attached to a robot housing 312. Robotic platform 310 may allow videoconferencing endpoint 300 to move in any direction. Videoconferencing endpoint 300 may include a robotic head 314 that supports a video camera 338 and a monitor 340. Robotic head 314 may allow a user to pan and tilt the video camera 338 and monitor 340 using pan and tilt actuators, as indicated by arrows 316 and 318. Robotic head 314, and robotic platform 310 may be referred to individually as robotic elements. Each of robotic head 314, and robotic platform 310 may operate in conjunction with a robotic driver that is configured to receive and implement instructions for controlling the various robotic elements.

Figure 4:
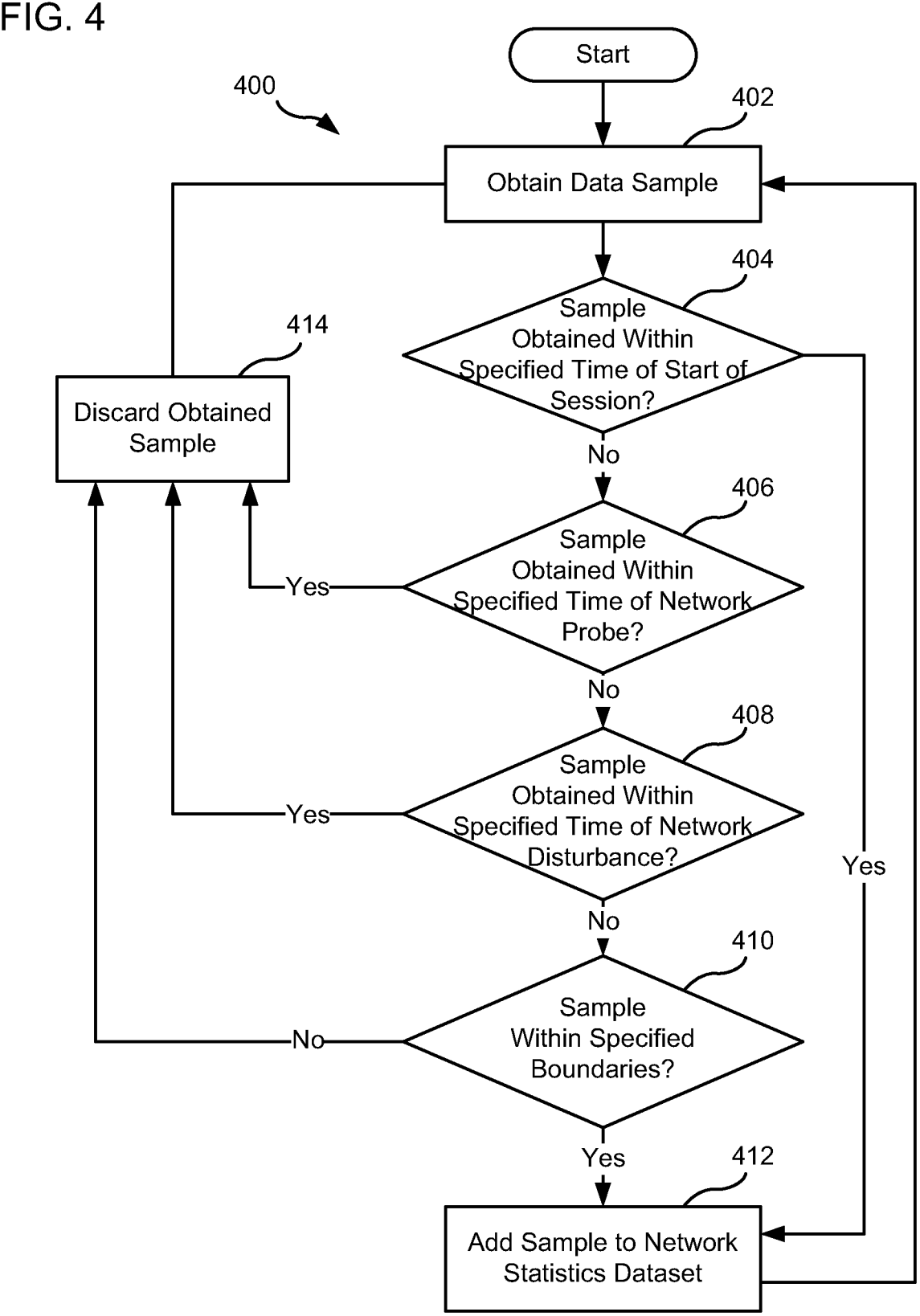
FIG. 4 illustrates one embodiment of a method of monitoring network statistics in a videoconferencing session and for determining which data samples are added to the network statistics dataset during a videoconferencing session.

FIG. 4 illustrates one embodiment of a method 400 for monitoring network statistics in a videoconferencing session and for determining which data samples are added to the network statistics dataset. The network statistics dataset may comprise a plurality of data samples that represent one or more quantifiable metrics of network conditions. Method 400 may be utilized during the entirety of a videoconferencing session between two or more videoconferencing endpoints. Accordingly, a network statistics dataset may be continually updated during a videoconference, and up-to-date information regarding network conditions may be utilized in connection with dynamic bandwidth allocation. According to various embodiments, such metrics may include, but are not limited to, measurements of latency, average data throughput, variations in latency over time, and the like. According to various embodiments, the network statistics dataset may include samples from the initiation of a videoconference, or only a trailing number of samples or minutes of samples.

A network statistics dataset may be established at the initiation of a session. In certain embodiments, an initial network statistics dataset may be created during an initial period in which data transmission occurs at a baseline rate. The baseline rate may be relatively minor in comparison to the theoretical throughput of the network connection between the endpoints. For example, a baseline rate in one embodiment may be established at the minimum allowable bandwidth for the endpoint, for example 150 kbps for outgoing data from endpoint 210 and 200 kbps for outgoing data from endpoint 202. The minimum allowable bandwidth has the highest probability of being stable for a given network connection. Such embodiments may allow for the creation of a robust network statistics dataset when the network connection between two or more endpoints is operating substantially below its theoretical throughput.

At 402, a data sample is obtained that represents at least one measurement of then-current network conditions. As discussed above, a data sample may, for example, comprise a measurement of latency, average data throughput, etc. In the present example, the measurement utilized is the latency associated with a ping; however, in other embodiments, similar principles may be utilized and adapted for analysis of other types of data samples. Method 400 determines at 404 whether the sample was obtained within a specified time of the start of a session. As discussed above, a network statistics dataset may be established at the initiation of the session during a period when the baseline transmission rate is significantly lower than the theoretical throughput of the network connection between the endpoints. Accordingly, if the data sample was obtained within the specified time of the start of a videoconferencing session, method 400 may proceed to determine whether the sample is within specified boundaries 410, as discussed in greater detail below.

After the passage of a specified amount time from the start of a session, method 400 may determine whether the sample was obtained within a specified time of a network probe 406. As the term is utilized herein, a network probe refers to an increase of bandwidth utilized by one or more endpoints participating in a videoconferencing session. The network probe may temporarily disturb a metric quantified by the obtained data sample, and accordingly, a sample obtained within a specified period following the network probe may be indicative of only a transitory state. According to various embodiments, a specified time may be established following a network probe during which data samples are discarded, so as to reduce the effects of such transitory samples on the network statistics dataset. If the data sample was obtained within the specified time of the network probe, the obtained sample may be discarded 414.

At 408, it may be determined whether the obtained data sample is within a specified time of a network disturbance. As the term is used herein, a network disturbance is in any event or circumstance, or combinations of events or circumstances, that temporarily affect a quantifiable metric representing network conditions. A network disturbance may include, for example, a disruption in data transmission, increased latency, increased bandwidth utilization by other users, etc. Following a network disturbance, the metric quantified by the obtained data sample may be indicative of only a transitory state. According to various embodiments, a specified time may be established following a network disturbance during which data samples are discarded, so as to reduce the effects of such transitory samples on the network statistics dataset.

At 410, the obtained data sample may be compared to specified boundaries relating to the network statistics dataset. For example, even under stable conditions, the latency of a plurality of data samples may differ significantly. In order to reduce the effect of aberrant data samples, certain criteria may be specified by a user or based on the data in the network statistics dataset. In one example, specified boundaries may exclude obtained data samples above the 90th percentile. Other boundaries may also be utilized. Further, other embodiments may utilize ranges in place of percentile boundaries.

Obtained data samples that are not discarded may then be added to the network statistics dataset at 412. Various criteria may be utilized (e.g., various time periods following the start of a session, a network probe, a network disturbance) to exclude certain obtained data samples from the network statistics dataset. Various criteria may be designed to minimize the influence of transitory conditions and other conditions which may not provide an accurate indication of the operation of the network system. According to one embodiment, the criteria may be specified so that approximately 90% of the obtained data samples included in the network statistics dataset are obtained during periods of relative stability on the network.

A network statistics dataset may be utilized by a videoconferencing system as an estimate of the available bandwidth of a particular network. Various thresholds may be established based upon the network statistics dataset, and one or more data values may be compared to the thresholds in order to determine whether a particular videoconferencing session is utilizing too much bandwidth or utilizing too little bandwidth. Latency may be utilized as one indicator of the condition of the network. According to one embodiment, bandwidth utilization of a videoconferencing system may be reduced when latency exceeds a specified threshold. For example, a system could reduce bandwidth usage whenever a latency measurement exceeds 350 milliseconds; however, a stable and high bandwidth connection may exceed 350 milliseconds ping time, and may result in a situation where the network connection is underutilized. According to other embodiments, a system dynamically managing bandwidth of a videoconferencing session may analyze a particular latency measurement with respect to percentile thresholds.

A network statistics dataset may be used to distinguish high latency and high bandwidth networks from networks exhibiting high latency because of network congestion. As described above, a network statistics dataset may include a plurality of the measurements. For example, a network statistics dataset may comprise a plurality of measurements of latency in a particular network. Analysis of the network statistics dataset may show latency measurements ranging from 100 milliseconds to 300 milliseconds, but 90% of latency measurements in the network statistics dataset are less than or equal to 115 milliseconds. Accordingly, 115 milliseconds may be established as a threshold value. Measurements exceeding 115 milliseconds may indicate network congestion, and may provide an indication of decreasing available bandwidth. According to other embodiments, a fixed offset may also be employed in order to avoid excluding data samples that only slightly exceed the threshold value. For example, a fixed offset of 30 milliseconds may be adopted. In embodiments utilizing a fixed offset, a network disturbance may not be recorded unless one or more data samples indicate a latency greater than the sum of the fixed offset and the threshold value. Embodiments including a fixed offset may provide greater tolerance for variation in latency, while reducing the risk of a false positive in identifying a network disturbance.

In a different example, latency measurements might range from 300 milliseconds to 420 milliseconds, with 90% of the latency measurements less than or equal to 330 milliseconds. In that example, a network disturbance would be detected when latency rises above 330 milliseconds. In this way, a system for dynamically allocating bandwidth adapts to stable high-latency connections.

As discussed above, an obtained data sample may be compared against specified boundaries in order to determine whether the obtained data sample should be included in a network statistics dataset. FIG. 5A illustrates an exemplary distribution 500 comprising a plurality of obtained data samples and specified boundaries that may be used in connection with various embodiments. In FIG. 5, the 70th and 90th percentiles of a normal distribution are shown. Depending upon where a particular measurement falls within distribution 500, a system may take various actions. For example, a data sample above the 90th percentile or some other specified percentile may be discarded. Discarding such samples may help to mitigate the effects of statistically aberrant obtained data samples. Data samples falling within these ranges may be referred to as excluded data samples.

Data samples falling between the 70th percentile and 90th percentile may not be immediately discarded, but such samples may not be immediately added to a network statistics dataset. Data samples falling within these ranges may be referred to as marginal data samples. Criteria may be specified in order to determine whether marginal data samples are discarded or added to a network statistics dataset. Various criteria may be associated with the evaluation of marginal data samples. For example, various embodiments may analyze a specified number of subsequently obtained data samples, or may analyze data samples obtained within a specified time (e.g., 60 seconds) before and/or after one or more marginal data samples is obtained.

According to one embodiment, specific criteria for evaluating marginal data samples may be based upon the results of subsequently obtained data samples. For example, a system may experience an increased latency of 100 ms, which arises over a period of 30 seconds. Without a sharp spike in latency, a network disturbance (e.g., the source of the additional latency) may not be recognized, and data samples representing the increased latency may be added to the network statistics dataset. If one or more subsequently obtained data samples within a specified period exceeds a specified threshold (e.g., the 90th percentile) the marginal data samples may be discarded. Subsequent data samples exceeding the specified threshold may indicate that the network is in an unstable condition, and that the marginal data samples do not reflect normal network conditions. If one or more subsequently obtained data samples within a specified period is below a specified threshold (e.g., the 70th percentile), the marginal data samples may be added to the network statistics dataset. Such a data sample may indicate that the marginal data samples reflect normal network conditions. Finally, if one or more subsequently obtained data samples within a specified period is between the 70th percentile and the 90th percentile, the marginal data samples may be included in the network statistics dataset.

Figure 5B:
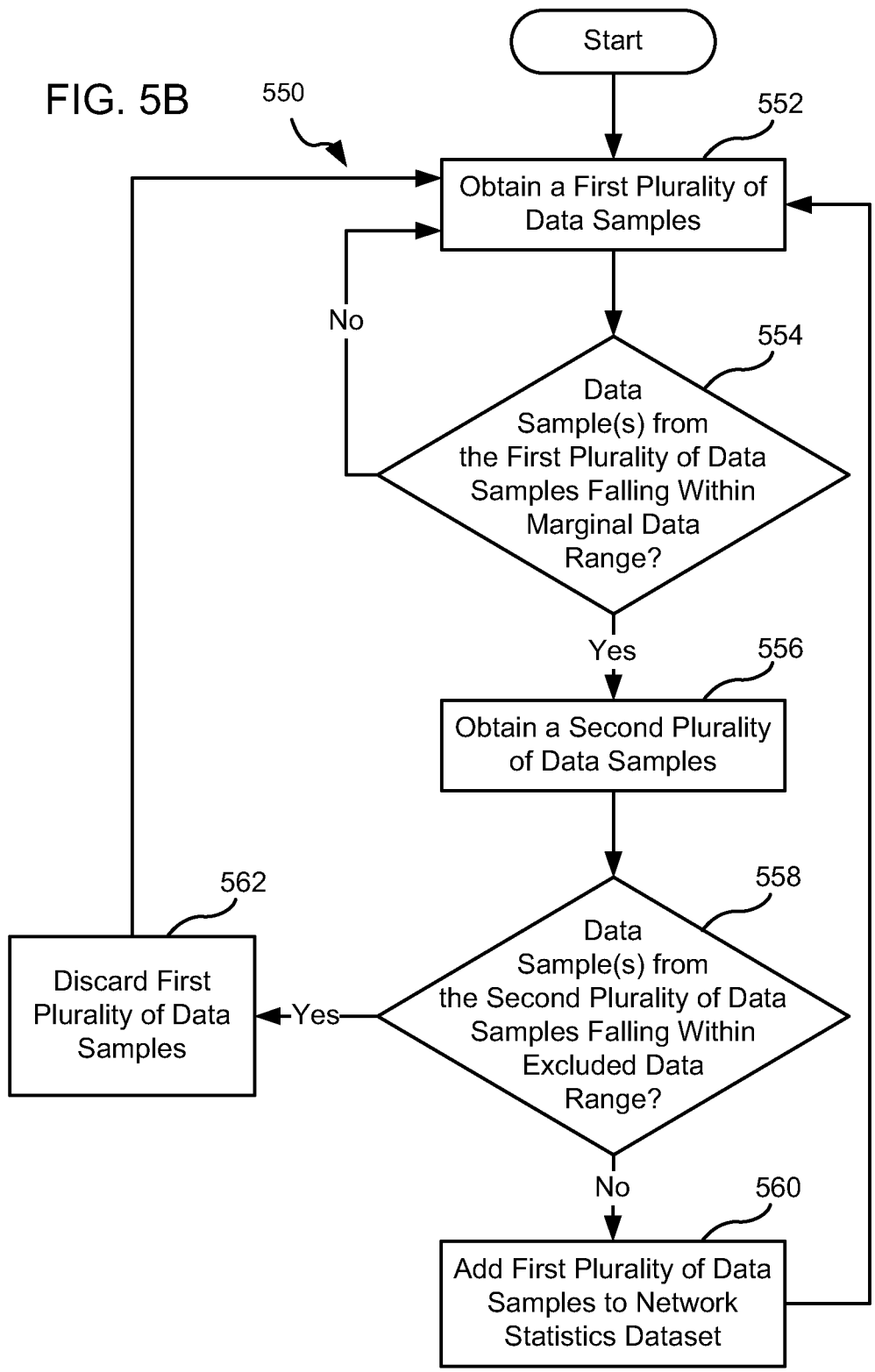
FIG. 5B illustrates one embodiment of a method for processing data samples that fall within a marginal data range.

FIG. 5B illustrates one embodiment of a method 550 for processing data samples that fall within a marginal data range. As discussed above, a marginal data range may be defined between an upper threshold and a lower threshold (e.g., the 90th percentile and the 70th percentile in FIG. 5A). At 552 a first plurality of data samples are obtained, and at 554, method 550 determines whether one or more data samples from the first plurality of data samples falls within the marginal data range. If so, a second plurality of data samples are obtained, at 556. At 558, the second plurality of data samples are analyzed to determine whether data samples from the second plurality of data samples fall within the excluded range. If so, the first plurality of data samples is discarded at 562. If no data samples from the second plurality of data samples fall within the excluded data range, the first plurality of data samples may be added to the network statistics dataset, at 560. In an alternative embodiment, upon receipt of each new sample the network statistics dataset is re-calculated based on the history of all samples collected since the start of the session, a trailing number of minutes, or sample set size.

Figure 6:
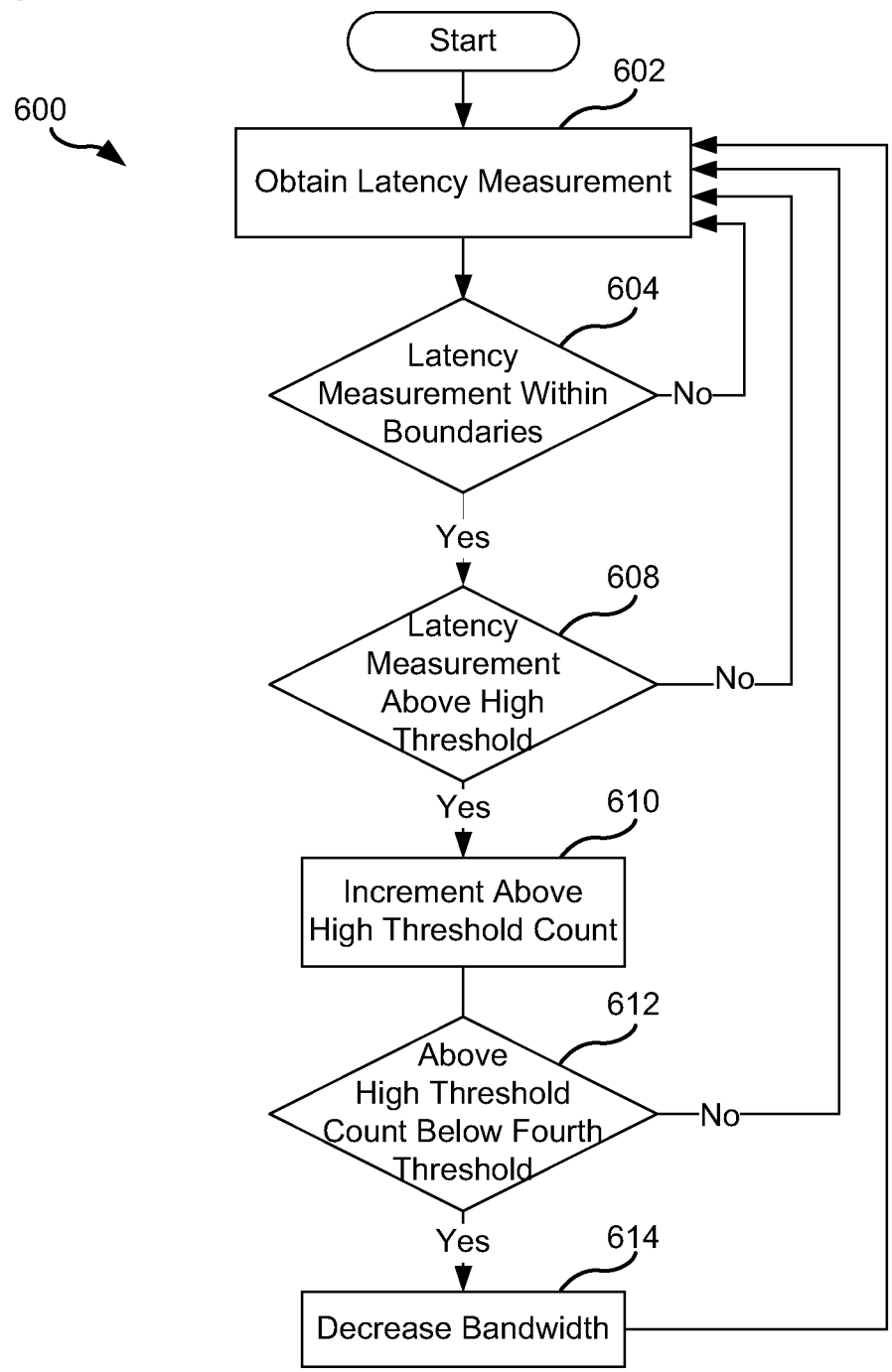
FIG. 6 illustrates one embodiment of a method for dynamically allocating bandwidth in a videoconferencing system.

FIG. 6 illustrates one embodiment of a method 600 for dynamically allocating bandwidth in a videoconferencing system. Method 600 illustrates an embodiment utilizing latency as a metric for evaluating network conditions. At 602, a latency measurement is obtained. It may be determined whether the obtained latency measurement is within specified boundaries, at 604. As discussed above, in connection with FIG. 5, measurements falling outside of specified ranges (e.g., above the 90th percentile) may be discarded. If the measurement falls outside of the specified boundaries, method 600 may return to 602 and obtain a new latency measurement. According to one embodiment, an increase in bandwidth may occur if a specified period of time has passed and no latency measurements have exceeded the high threshold. In this embodiment, the system presumes that because a network has remained stable for a specified time, additional bandwidth may be utilized.

It may be determined at 608 whether the latency measurement is above a high threshold. A latency measurement exceeding the high threshold may be indicative of a network disruption. Accordingly, at 610, an above high threshold count may be incremented. At 612, the above high threshold count may be compared to a fourth threshold. A fourth threshold may specify the number of above high threshold events that are detected before decreasing bandwidth, at 614.

Figure 7:
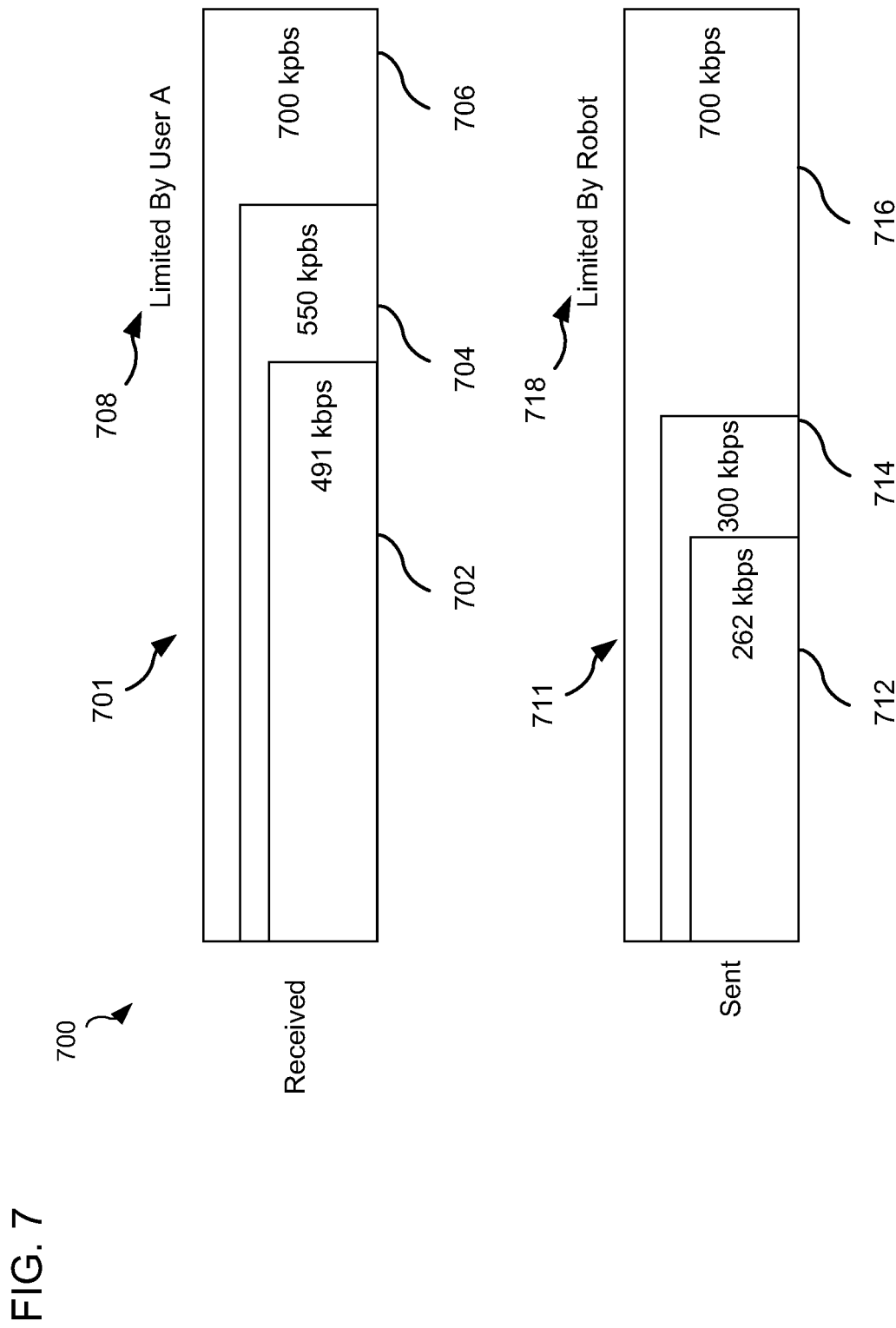
FIG. 7 illustrates a graphical user interface for displaying bandwidth utilization and dynamically established incoming and outgoing maximum bandwidth thresholds.

FIG. 7 illustrates a graphical user interface 700 for displaying bandwidth utilization and dynamically established incoming and outgoing maximum bandwidth thresholds. According to various embodiments, one or more videoconferencing endpoints may display graphical user interface 700. Information regarding data being received may be displayed by a first bar graph 701, while information regarding data being sent may be displayed by a second bar graph 711. Each of bar graphs 701 and 711 may show a first bar 702 and 712, respectively, which illustrate a current data transmission rate. Bar graphs 701 and 711 may also show a second bar 704 and 714, respectively, which illustrate bandwidth allocation. Bars 702 and 712 are less than or equal to the bandwidth allocation shown by bar 704 and 714. Bar graphs 701 and 711 may also illustrate a maximum throughput 706 and 716, respectively, based on the network connection between two or more videoconferencing endpoints.

Bar graphs 701 and 711 may also include an indication 708 and 718, respectively, that shows a limiting component in the network. For example, a multicasting session might include a local user, User A (a remote user), and a robotic videoconferencing endpoint. The data transmission rate from the robotic videoconferencing endpoints may be limited to the minimum value that can be sent or received from the other videoconferencing endpoints. In the illustrated embodiment, the limit for receiving data is imposed by User A, while the limit for transmitting data is imposed by the robotic videoconferencing endpoint. In one embodiment, the designated limiting endpoint may only be displayed when a mouse cursor is hovered over the related bar graph.

FIG. 8 illustrates a functional block diagram of one embodiment of a system 800, including a videoconferencing endpoint 810 and a robotic videoconferencing endpoint 850.

System 800 allows videoconferencing endpoint 810 to exchange video, audio, and other types of data with robotic videoconferencing endpoint 850.

Videoconferencing endpoint 810 includes a network connection 822, Random Access Memory (RAM) 824, processor 826, input/output ports 828, a display driver 830, a computer readable storage medium 812, and a bus 820. Bus 820 provides a connection between network connection 822, RAM 824, processor 826, and computer readable storage medium 812. Processor 826 may be embodied as a general purpose processor, an application specific processor, a microcontroller, a digital signal processor, or other similar device. Processor 826 performs logical and arithmetic operations based on program code stored within RAM 824 and/or computer readable storage medium 812.

Network connection 822 may be configured to communicate with robotic videoconferencing endpoint by way of one or more network components, such as firewall 840, network 842, firewall 844, and wireless data transceiver 846. Network connection 822 may facilitate communication using any number of available protocols and/or physical media. Network 842 may comprise an intranet, a virtual private network, or a public network, such as the Internet or other data communications networks (e.g., cellular data networks). Firewalls 840 and 844 may be disposed between videoconferencing endpoints 810 and 850. According to various embodiments, network management techniques may be utilized to successfully route data from videoconferencing endpoint 810 to robotic videoconferencing endpoint 850.

Input/output ports 828 may be configured to allow videoconferencing endpoint 810 to utilize a wide variety of peripheral devices, some of which may generate data to be transmitted to robotic videoconferencing endpoint 850. For example, peripheral devices which may be utilized may include a video camera, a microphone, a device for controlling the movement of robotic videoconferencing endpoint 850, a keyboard, a mouse, and other such devices. Input/output ports 828 may comprise a variety of types of ports, such as USB, serial, parallel, IEEE 1394, and the like.

Display driver 830 may facilitate the generation of video images to be displayed to a user videoconferencing endpoint 810. Display driver 830 may, according to various embodiments, generate video data received from robotic videoconferencing endpoint 850 and display such data to a user. Display driver 830 may also be responsible for interfacing with other display devices, for example a touch screen.

Computer readable storage medium 812 may comprise various modules for communicating with robotic videoconferencing endpoint 850. Such modules may include a bandwidth allocation module 814, and encoding/decoding module 816, a network statistics dataset module 818, and a data prioritization module 819. Each module may perform one or more tasks associated with communication with robotic video endpoint 850 and/or management of such communications. In alternative embodiments, more or fewer modules than are shown in FIG. 8 may be utilized.

Bandwidth allocation module 814 may be configured to monitor and dynamically adjust the bandwidth utilized for transmission of data between videoconferencing endpoint 810 and robotic videoconferencing endpoint 850. As discussed above, a variety of methods may be utilized for dynamically allocating and adjusting bandwidth. Bandwidth allocation module 814 may be configured to implement the various methods for bandwidth allocation disclosed herein. Bandwidth allocation module 814 may further be configured to generate a graphical user interface display, such as illustrated in FIG. 7, for displaying bandwidth utilization and dynamically established incoming and outgoing maximum bandwidth thresholds.

Encoding/decoding module 816 may be configured to encode and/or decode video data, audio data, control data, and status data exchanged between videoconferencing endpoint 810 and robotic videoconferencing endpoint 850. According to various embodiments, encoding/decoding module 816 may be configured to adjust the video frame rate, image quality, compression ratios, and other characteristics of data to be transmitted in order to conform data transmission rates to an allocated bandwidth. According to one particular embodiment, encoding/decoding module 816 may adjust a video frame rate prior to segmenting the data into data packets.

Network statistics dataset module 818 may be configured to generate a network statistics dataset and to selectively add data to the network statistics dataset. Various embodiments for generating and adding data to the network statistics dataset are disclosed herein, and network statistics dataset module 818 may be configured to perform the features described in connection with such embodiments.

Data prioritization module 819 may be configured to prioritize various types of data to be transmitted between videoconferencing endpoint 810 robotic videoconferencing endpoint 850. According to various embodiments, a variety of data prioritization schemes may be employed so that higher priority data is transmitted with greater reliability or at a higher data rate than lower priority data. For example, in system 800 control data transmitted from videoconferencing endpoint 810 to robotic videoconferencing endpoint 850 may be designated as high priority data. Such a prioritization may allow a user to remain in control of the motion of robotic videoconferencing endpoint 850 even if network throughput is reduced. Status data, which may include telemetry data gathered from a patient (e.g., pulse rate, EKG, oxygenation, etc.), may also be designated as relatively high priority data. Audio data may be prioritized before video data, such that a medical practitioner and patient can maintain audible communication in spite of decreases in network throughput. Finally, video data may be transmitted using the lowest priority.

According to various embodiments, videoconferencing endpoint 810 may be embodied as a general purpose computer including particular software and/or configured to interface with robotic videoconferencing endpoint 850. Such software may be delivered as a computer program product. Hardware resources facilitating communication with and/or control of robotic videoconferencing endpoint 850 may, according to various embodiments, comprise an audio and/or video input device coupled to input/output ports 828, or an input device specifically configured to control one or more robotic elements of robotic videoconferencing endpoint 850.

Robotic videoconferencing endpoint 850 includes a robotics driver 854, a display driver 856, RAM 858, a processor 860, input/output ports 862, a wireless data transceiver 864, a computer readable storage medium 852, and a bus 876. The function of display driver 856, RAM 858, and processor 860 may be similar to the functions described in connection with corresponding structures in videoconferencing endpoint 810. Input/output ports 862 may further be configured to receive telemetry data from a variety of sensors, which may be utilized to monitor various physical conditions. In one particular embodiment, where robotic videoconferencing endpoint 850 is utilized in a telemedicine application, input/output ports 862 may be configured to interface with a variety of medical sensors (e.g., pulse rate sensor, an EKG sensor, a blood oxygenation sensor, etc.).

Robotics driver 854 may be configured to receive and implement instructions for moving robotic videoconferencing endpoint 850. Such instructions may include driving robotic videoconferencing endpoint 850 from one place to another, manipulating one or more robotic arms, and the like.

Wireless data transceiver 864 may be configured to exchange data wirelessly with wireless data transceiver 846. Data may be exchanged according to a variety of wireless protocols, including but not limited to the IEEE 802.11 protocols and cellular data transmission protocols.

Computer readable storage medium 852 may comprise various modules for communicating with videoconferencing endpoint 810. Such modules may include a bandwidth allocation module 866, and encoding/decoding module 868, a network statistics dataset module 870, a robotic control module 872, and a data prioritization module 874. The functions of bandwidth allocation module 866, encoding/decoding module 868, network statistics dataset module 870, and data prioritization module 874 may be similar to corresponding modules, which are described above in connection with videoconferencing endpoint 810.

Robotic control module 872 may operate in conjunction with robotics driver 854 to facilitate control of robotic videoconferencing endpoint 850. Robotic control module 872 may be configured, according to various embodiments, to interact with one or more devices associated with videoconferencing endpoint 810 and to receive instruction from such device that allows a remote user to control robotic videoconferencing endpoint 850.

Many changes may be made to the details of the above-described embodiments without departing from the underlying principles of the present disclosure. The scope of the present invention should, therefore, be determined only by the following claims.

The invention claimed is:

1. A method of adjusting a bandwidth utilization between a first endpoint and a second endpoint in a videoconferencing session, comprising:
   generating a network statistics dataset comprising a first plurality of data samples, each of the plurality of data samples comprising a quantifiable metric representing network conditions;
   establishing a first threshold-based analysis of the network statistics dataset;
   obtaining a second plurality of data samples;
   comparing each of the second plurality of data samples to the network statistics dataset;
   identifying a first specified number of data samples from among the second plurality of data samples that fall above the first threshold;
   decreasing a total transmission rate between a first endpoint and a second endpoint in a videoconferencing session; and
   establishing, based on the network statistics dataset, a first minimum allowable transmission rate from the first endpoint to the second endpoint and a second minimum allowable transmission rate from the second endpoint to the first endpoint, wherein the first minimum allowable transmission rate and the second minimum allowable transmission rate are different.

2. The method of claim 1, wherein the first threshold corresponds to the 70th percentile of data samples in the network statistics dataset.

3. The method of claim 1, further comprising:
   obtaining a third plurality of data samples;
   comparing each of the third plurality of data samples to the network statistics dataset;
   identifying a second specified number of data samples from among the third plurality of data samples that fall below a second threshold; and
   increasing the total transmission rate between the first endpoint and the second endpoint in the videoconferencing session.

4. The method of claim 1, further comprising:
   obtaining a third plurality of data samples;
   comparing each of the third plurality of data samples to the network statistics dataset;
   identifying fewer than the first specified number of data samples from among the third plurality of data samples that fall above the first threshold; and
   increasing the total transmission rate between the first endpoint and the second endpoint in the videoconferencing session.

5. A method of adjusting a bandwidth utilization between a first endpoint and a second endpoint in a videoconferencing session, comprising:
   initiating a videoconferencing session between a first endpoint and a second endpoint via a network;
   transmitting data between the first endpoint and the second endpoint at a fixed first total transmission rate during a first period of the videoconferencing session;
   collecting a first plurality of data samples during the first period in a network statistics dataset, each of the plurality of data samples comprising a quantifiable metric representing network conditions;
   creating a network statistics dataset from the first plurality of data samples;
   establishing a second total transmission rate based on an analysis of the network statistics dataset, the second total transmission rate exceeding the first total transmission rate;
   transmitting data between the first endpoint and the second endpoint at the second total transmission rate during the second period of the videoconferencing session; and
   establishing, based on the network statistics dataset, a first minimum allowable transmission rate from the first endpoint to the second endpoint and a second minimum allowable transmission rate from the second endpoint to the first endpoint, wherein the first minimum allowable transmission rate and the second minimum allowable transmission rate are different.

6. The method of claim 5, further comprising:
   collecting a second plurality of data samples during the second period of the videoconferencing session;
   discarding data samples from the second plurality of data samples that exceed a first percentile of the data samples in the network statistics dataset;
   adding remaining data samples from the second plurality of data samples to the network statistics dataset.

7. The method of claim 5, wherein the first percentile is approximately equal to the 90th percentile of data samples in the network statistics dataset.

8. The method of claim 5, wherein the first plurality of data samples comprises a plurality of latency measurements.

* * * * *